United States Patent
Fukui

(10) Patent No.: US 10,438,382 B2
(45) Date of Patent: Oct. 8, 2019

(54) IMAGE PROCESSING APPARATUS AND IMAGE PROCESSING METHOD

(71) Applicant: CANON KABUSHIKI KAISHA, Tokyo (JP)

(72) Inventor: Toshifumi Fukui, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 64 days.

(21) Appl. No.: 15/917,951

(22) Filed: Mar. 12, 2018

(65) Prior Publication Data
US 2018/0276855 A1 Sep. 27, 2018

(30) Foreign Application Priority Data
Mar. 27, 2017 (JP) ................. 2017-061164

(51) Int. Cl.
*G06K 9/00* (2006.01)
*G06T 11/00* (2006.01)
(Continued)

(52) U.S. Cl.
CPC .......... *G06T 11/008* (2013.01); *A61B 5/0095* (2013.01); *G06T 5/00* (2013.01); *G06T 5/003* (2013.01); *G06T 7/0012* (2013.01); *G06T 15/08* (2013.01); *A61B 2576/00* (2013.01); *G06T 2207/10072* (2013.01); *G06T 2207/10084* (2013.01); *G06T 2207/20024* (2013.01); *G06T 2207/30024* (2013.01); *G06T 2207/30088* (2013.01); *G06T 2207/30101* (2013.01); *G06T 2207/30104* (2013.01)

(58) Field of Classification Search
CPC . A61B 2576/00; A61B 5/0095; G06T 11/008; G06T 15/08; G06T 2207/10084; G06T 2207/20024; G06T 2207/30024; G06T 2207/30088; G06T 2207/30101; G06T 2207/30104; G06T 5/003; G06T 7/0012; G06T 2207/10072; G06T 5/00

See application file for complete search history.

(56) References Cited

U.S. PATENT DOCUMENTS

2005/0240094 A1* 10/2005 Pichon ...................... G06T 7/60
                                                                                600/407
2009/0073257 A1*  3/2009 Tanaka .................. G06T 7/0012
                                                                                348/45

(Continued)

FOREIGN PATENT DOCUMENTS

JP 2013-176414 A 9/2013

*Primary Examiner* — Tom Y Lu
(74) *Attorney, Agent, or Firm* — Venable LLP

(57) ABSTRACT

An image processing apparatus, comprises an information acquiring unit that acquires three-dimensional data representing characteristic information on an object at a plurality of voxels; a shape information acquiring unit that acquires information on a surface shape of the object; a distance calculating unit that calculates, for each of the voxels, a distance between a surface of the object and a position inside the object corresponding to the voxel, based on the information on the surface shape; a filtering unit that performs, for each of the voxels, filtering processing, including blur processing in accordance with the calculated distance; and an image generating unit that generates a two-dimensional image, based on the three-dimensional data after the filtering processing.

15 Claims, 7 Drawing Sheets

(51) Int. Cl.
*G06T 7/00* (2017.01)
*G06T 15/08* (2011.01)
*G06T 5/00* (2006.01)
*A61B 5/00* (2006.01)

(56) References Cited

U.S. PATENT DOCUMENTS

| | | | |
|---|---|---|---|
| 2010/0201687 A1* | 8/2010 | Breeuwer | G06T 15/08 345/424 |
| 2011/0091086 A1* | 4/2011 | Seko | A61B 8/463 382/131 |
| 2011/0149680 A1* | 6/2011 | Oishi | A61B 6/56 367/7 |
| 2011/0216951 A1* | 9/2011 | Ye | G06T 7/0012 382/128 |
| 2013/0109963 A1* | 5/2013 | Zhu | A61B 8/0825 600/427 |
| 2014/0371571 A1 | 12/2014 | Tsujita | |

* cited by examiner

IMAGE PROCESSING APPARATUS AND IMAGE PROCESSING METHOD

BACKGROUND OF THE INVENTION

Field of the Invention

The present invention relates to an apparatus that processes an image acquired by imaging an object.

Description of the Related Art

In recent years, research on the imaging of structural information and physiological information—functional information—inside an object is progressing in medical fields. As one such technique, photoacoustic tomography (PAT) has been proposed lately.

When a living body (object) is irradiated with light, such as a laser beam, an acoustic wave (typically an ultrasonic wave) is generated when the light is absorbed by a bio-tissue inside the object. This phenomena is called a "photoacoustic effect", and an acoustic wave generated by the photoacoustic effect is called a "photoacoustic wave". Each tissue constituting the object has a different absorption rate of the light energy, therefore the sound pressure of the photoacoustic wave generated from each tissue is also different. In PAT, the generated photoacoustic wave is received by a probe, and the received signal is mathematically analyzed, whereby the characteristic information inside the object can be acquired.

The characteristic information is the distribution of optical characteristic values, such as an initial sound pressure distribution, an optical absorption energy density distribution, and an optical absorption coefficient distribution. By acquiring this information using light with a plurality of wavelengths, the concentration of a specific substance inside the object (e.g. hemoglobin concentration in blood, oxygen saturation degree of blood) can be quantitatively measured.

In photoacoustic tomography, the object information can be acquired as three-dimensional information.

Normally an image is displayed on a two-dimensional plane, hence the three-dimensional information must be projected on the two-dimensional plane. Known methods of converting the three-dimensional data acquired by measuring an object into a two-dimensional image are, for example, a maximum intensity projection method in which a voxel having a maximum intensity in the depth direction is projected, and a surface rendering method in which only a signal located closest to the viewpoint is visualized.

Japanese Patent Application Publication No. 2013-176414 discloses a method of projecting a three-dimensional image data acquired by photoacoustic tomography onto a two-dimensional plane using the maximum intensity projection method.

SUMMARY OF THE INVENTION

A problem of the method disclosed in Japanese Patent Application Publication No. 2013-176414 is that the information in the depth direction cannot be distinguished very well when the three-dimensional data is converted into a two-dimensional image.

With the foregoing in view, it is an object of the present invention to provide an image in which the information in the depth direction can be easily distinguished using an image processing apparatus configured to convert the three-dimensional data into a two-dimensional image.

The present invention in its one aspect provides an image processing apparatus, comprising an information acquiring unit that acquires three-dimensional data representing characteristic information on an object at a plurality of voxels; a shape information acquiring unit that acquires information on a surface shape of the object; a distance calculating unit that calculates, for each of the voxels, a distance between a surface of the object and a position inside the object corresponding to the voxel, based on the information on the surface shape; a filtering unit that performs, for each of the voxels, filtering processing, including blur processing in accordance with the calculated distance; and an image generating unit that generates a two-dimensional image, based on the three-dimensional data after the filtering processing.

The present invention in its another aspect provides an image processing method, comprising an information acquiring step of acquiring three-dimensional data representing characteristic information on an object at a plurality of voxels; a shape information acquiring step of acquiring information on a surface shape of the object; a distance calculating step of calculating, for each of the voxels, a distance between a surface of the object and a position inside the object corresponding to the voxel, based on the information on the surface shape, a filtering step of performing, for each of the voxels, filtering processing, including blur processing in accordance with the calculated distance; and an image generating step of generating a two-dimensional image, based on the three-dimensional data after the filtering processing.

According to the present invention, an image in which the information in the depth direction can be easily distinguished can be provided using an image processing apparatus configured to convert the three-dimensional data into a two-dimensional image.

Further features of the present invention will become apparent from the following description of exemplary embodiments with reference to the attached drawings.

DESCRIPTION OF THE EMBODIMENTS

Figure 1:
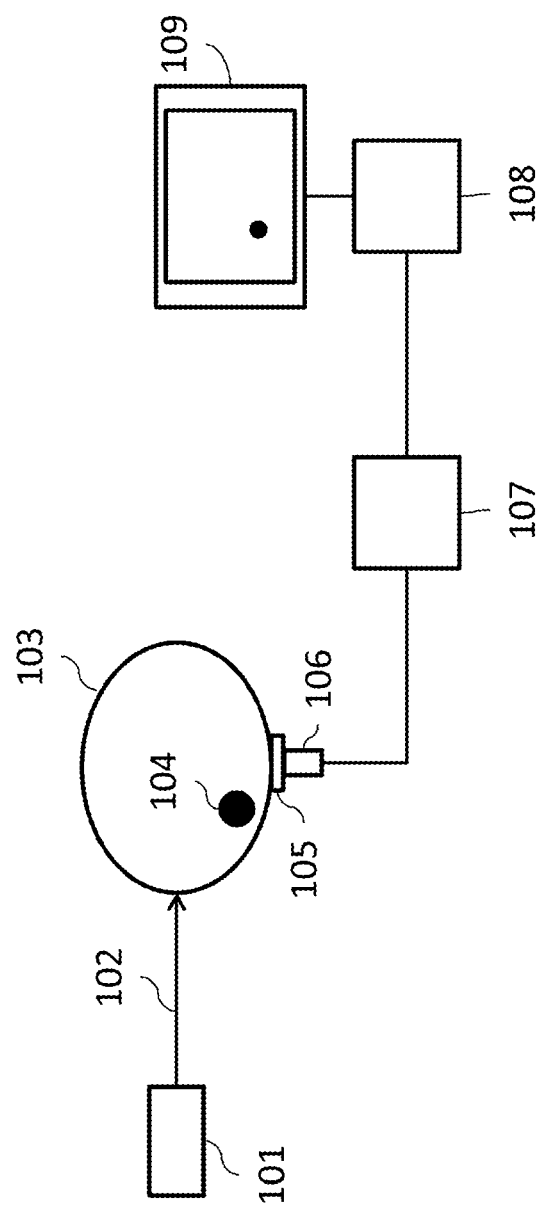
FIG. 1 is a diagram depicting the functional blocks of an object information acquiring apparatus according to Embodiment 1.

Preferred embodiments of the present invention will be described with reference to the drawings. The dimensions, materials, and shapes of the components and the relative positions thereof, which will be described below, can be appropriately changed depending on the configuration and various conditions of an apparatus to which the invention is applied. Therefore the following description is not intended to limit the scope of the invention.

The present invention relates to a technique to convert the characteristic information inside an object, generated based on an acoustic wave propagated from the object, into a two-dimensional image. This means that the present invention may be understood as an image processing apparatus or an image processing method. The present invention may also be understood as an object information acquiring apparatus that includes this image processing apparatus, or an object information acquiring method that includes this image processing method.

Further, the present invention may be understood as a program which causes an information processing apparatus equipped with such hardware resources as a CPU and memory to execute these methods, or a storage medium storing the program, or an information processing apparatus.

The image processing apparatus of the present invention can be applied to an apparatus which receives an acoustic wave, which is generated inside an object when the object is irradiated with light (electromagnetic wave), and acquires the characteristic information of the object as an image data utilizing the photoacoustic effect. In this case, the characteristic information is information on a characteristic value, which corresponds to each of a plurality of positions and is generated using a received signal acquired by receiving the photoacoustic wave.

The characteristic information acquired by the photoacoustic measurement is a value reflecting the absorption rate of light energy. For example, the characteristic information includes: a generation source of an acoustic wave which was generated by irradiating light; an initial sound pressure inside the object; a light energy absorption density and absorption coefficient which are derived from the initial sound pressure; and a concentration of a substance constituting a tissue. If an oxyhemoglobin concentration and a deoxyhemoglobin concentration are determined as the substance concentration, an oxygen saturation distribution can be calculated. A glucose concentration, a collagen concentration, a melanin concentration, a volume fraction of fat or water and the like may also be determined.

Based on the characteristic information at each position inside the object, a two-dimensional or a three-dimensional characteristic information is acquired. The distribution data can be generated as image data. The characteristic information may be determined as distribution information at each position inside the object, instead of as numeric data. In other words, such distribution information as initial sound pressure distribution, energy absorption density distribution, absorption coefficient distribution, and oxygen saturation distribution may be determined.

The acoustic wave referred to in this description is typically an ultrasonic wave, and includes an elastic wave called a "sound wave" and an "acoustic wave". An electric signal converted from an acoustic wave by a probe or the like is called an "acoustic signal". The ultrasonic wave or acoustic wave that is referred to in this description is not intended to limit the wavelength of this elastic wave. An acoustic wave generated by the photoacoustic effect is called a "photoacoustic wave" or a "light-induced ultrasonic wave". An electric signal which originates from a photoacoustic wave is also called a "photoacoustic signal".

Embodiment 1

<System Configuration>

FIG. 1 is a functional block diagram depicting a configuration of an object information acquiring apparatus according to Embodiment 1. The object information acquiring apparatus according to Embodiment 1 is a photoacoustic apparatus, and includes a light source 101, an optical system 102, an acoustic matching material 105, an acoustic wave probe 106, a signal processing unit 107, a data processing unit 108, and a displaying unit 109. The reference number 103 denotes an object, and the reference number 104 denotes a light absorber.

Object 103

An object 103 does not constitute part of the object information acquiring apparatus according to this embodiment, but will be described first. The object information acquiring apparatus according to this embodiment is an apparatus that performs diagnosis of, for instance, malignant cancers, vascular diseases, and blood-sugar levels of humans and animals, and performs follow up observation of chemotherapy. This means that a possible object is a living body part, such as a breast, finger and limb of humans and animals.

Inside the object, a light absorber having a high light absorption coefficient, such as water, fat, protein, oxyhemoglobin and deoxyhemoglobin, exists in the case of a living body, hence a photoacoustic wave is generated due to light irradiation. In the case of using a phantom as the object, a substance simulating the optical characteristic is sealed inside as the light absorber, whereby the photoacoustic wave is generated and measured.

Light Source 101

The light source 101 is an apparatus to generate pulsed light irradiated to an object. The light source is preferably a laser light source in order to acquire high power, but a light-emitting diode, a flash lamp or the like may be used instead of a laser. In the case of using a laser as the light source, various lasers, such as a solid-state laser, a gas laser, a dye laser and a semiconductor laser can be used.

The wavelength of the pulsed light is preferably a specific wavelength with which the pulsed light is absorbed by a specific component out of the components constituting the object, and is a wavelength with which the light propagates into the object. In concrete terms, such a wavelength is at least 700 nm and not more than 1200 nm if the object is a living body. The light in this region can reach a relatively deep region of the living body, and information in the deep region can be acquired.

To effectively generate the photoacoustic wave, the light must be irradiated in a sufficiently short time in accordance with the thermal characteristic of the object. When the object is a living body, not more than several tens of nano seconds are suitable as the pulse width of the pulsed light generated from the light source.

The timing, waveform, intensity and the like of the light irradiation are controlled by a controlling unit (not illustrated).

Optical System 102

The optical system 102 is a system to transmit pulsed light emitted from the light source 101. The light emitted from the light source is guided to the object while being processed into a predetermined light distribution form by such an optical component as a lens and mirror, and the object is irradiated with the light. The light may be propagated using an optical waveguide, such as optical fiber.

The optical system 102 may include optical components, such as a lens, a mirror, a prism, optical fiber, a diffuser and a shutter. These optical components may be any component as long as the object can be irradiated with the light emitted from the light source in a desired shape of the light. In terms of safety to a human body and increasing the diagnostic region, it is preferable to spread the light over a certain area, rather than condensing the light by a lens.

Acoustic Wave Probe 106

The acoustic wave probe 106 is an element that receives an acoustic wave from inside the object 103, and converts the acoustic wave into an electric signal. An acoustic wave detecting element is also called a probe, an acoustic wave probe, an acoustic wave detector, an acoustic wave receiver, or a transducer.

The acoustic wave generated from a living body is an ultrasonic wave in the 100 KHz to 100 MHz range, hence an element that can receive this frequency band is used for the acoustic wave detecting element. In concrete terms, a transducer using piezoelectric phenomena, a transducer using a resonance of light, a transducer using a change of capacitance or the like can be used.

It is preferable that the acoustic element has high sensitivity and a wide frequency band. For example, a piezoelectric element using lead zirconate titanate (PZT) and an acoustic element using a high polymer piezoelectric film material, such as polyvinylidene fluoride (PVDF), capacitive micro-machine ultrasonic transducer (CMUT), and a Fabry-Perot interferometer, can be used. However, the acoustic element is not limited to these elements, but may be any element as long as a function of a probe can be implemented.

The acoustic matching material 105, which is a material to match acoustic impedance, is disposed between the acoustic wave probe 106 and the object 103. For the acoustic matching material 105, gel, water, oil or the like can be used.

The signal processing unit 107 is a unit that amplifies an acquired electric signal, and converts the electric signal into a digital signal.

The signal processing unit 107 may be constituted by an amplifier that amplifies a received signal, an A/D converter which converts a received analog signal into a digital signal, a memory implementing FIFO that stores a received signal, and an arithmetic circuit such as an FPGA chip. The signal processing unit 107 may be constituted by a plurality of processors and arithmetic circuits.

The data processing unit 108 is a unit that acquires object information inside the object, such as a light absorption coefficient and an oxygen saturation degree, based on the converted digital signal (hereafter called "photoacoustic signal"). In concrete terms, the data processing unit 108 generates the three-dimensional initial sound pressure distribution inside the object from the collected electric signals. To generate the initial sound pressure distribution, a universal back-projection (hereafter called "UBP") algorithm or a delay and sum algorithm, for example, can be used.

The data processing unit 108 also generates a three-dimensional light intensity distribution inside the object based on the information on the quantity of light irradiated to the object. The three-dimensional light intensity distribution can be acquired by solving the light diffusion equation based on the information on the two-dimensional light intensity distribution. The absorption coefficient distribution inside the object can be acquired using the initial sound pressure distribution inside the object generated from the photoacoustic signal and the three-dimensional light intensity distribution. Further, the oxygen saturation distribution inside the object can be acquired by computing the absorption coefficient distribution at a plurality of wavelengths.

Furthermore, the data processing unit 108 converts the three-dimensional absorption coefficient distribution into the two-dimensional image using the later mentioned method.

The data processing unit 108 corresponds to a shape information acquiring unit, a distance calculating unit, an image generating unit, and a display controlling unit according to the present invention.

The data processing unit 108 may be constituted by a computer, which includes a CPU, a RAM, a non-volatile memory, and a control port. Each module is controlled by programs stored in the non-volatile memory and executed by the CPU. The data processing unit 108 may be a general purpose computer or a custom-designed workstation.

The unit that performs the computing functions of the data processing unit 108 may be constituted by such a processor as a CPU and graphics processing unit (GPU), and such an arithmetic circuit as a field programmable gate array (FPGA) chip. Each of these units may be constituted by a single processor or arithmetic circuit, or may be constituted by a plurality of processors and arithmetic circuits.

The unit that performs the storing function of the data processing unit 108 may be a non-transitory storage medium, such as a read only memory (ROM), a magnetic disk and a flash memory, or a volatile medium, such as a random access memory (RAM). The storage medium in which programs are stored is a non-transitory storage medium. Each of these units may be constituted by one storage medium, or may be constituted by a plurality of storage media. The unit that performs the control function for the data processing unit 108 is constituted by an arithmetic element, such as a CPU.

The displaying unit 109 is a unit that displays information acquired by the data processing unit, and displays the processed information thereof, and is typically a display device. The displaying unit 109 may include a plurality of displaying units, so that parallel display can be performed.

<Method of Measuring Object>

A method of measuring a living body (object) using the object information acquiring apparatus according to this embodiment will be described.

The object 103 is irradiated with first pulsed light emitted from the light source 101. When a part of the energy of the light, which propagates inside the object, is absorbed by a light absorber, such as blood, an acoustic wave is generated from this light absorber by thermal expansion. When a cancer exists inside the living body, the light is specifically absorbed by the newly generated blood vessels of the cancer, in the same manner as the blood in other normal segments, and an acoustic wave is generated. The acoustic wave generated inside the living body is received by the acoustic wave probe 106.

The signal received by the acoustic wave probe 106 is converted by the signal processing unit 107, and is then analyzed by the data processing unit 108. The analysis result is converted into the image data which represents the characteristic information inside the living body (e.g. initial sound pressure distribution, absorption coefficient distribution), and is outputted via the displaying unit 109. In this embodiment, the data processing unit 108 first generates the three-dimensional data which represents the absorption coefficient distribution, then converts this three-dimensional data into a two-dimensional image, and outputs this image to the displaying unit 109.

Figure 2:
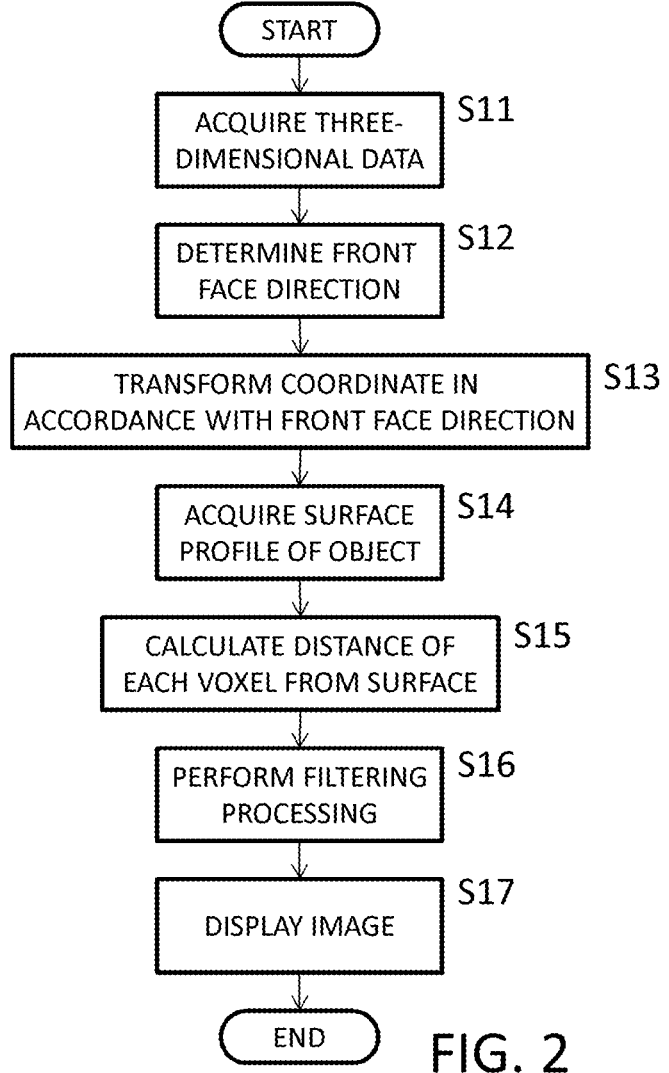
FIG. 2 is a flow chart depicting processing to convert object information into a two-dimensional image.

Now the method of data processing unit 108 converting an acquired three-dimensional absorption coefficient distribution (hereafter called "three-dimensional data") into a two-dimensional image will be described. FIG. 2 is a flow chart depicting the processing performed by the data processing unit 108.

First in step S11, the three-dimensional data (object information) is acquired. This three-dimensional data is data expressed by voxels in the three-dimensional space. In this embodiment, the coordinates in the three-dimensional space, corresponding to the object information, are expressed as (X, Y, Z).

Then in step S12, the direction of the front face of the object 103 (front face direction) is determined. The front face direction is a direction where the view point of the user, who provides the object image, is located in the three-dimensional space. This direction may be fixed or may be changed in accordance with the input by the user (e.g. operation to move/rotate the object on screen).

Then in step S13, the coordinate system based on the location of the viewpoint of the user is set, so as to transform the coordinates of the three-dimensional data. In this case, a coordinate system, constituted by the Z axis (axis parallel with the front face direction which was set) and the X and Y axes which are perpendicular to the Z axis, is set, whereby the coordinates of the three-dimensional data are transformed. Here it is assumed that the positive direction of the Z axis is the side of the viewpoint of the user. The coordinates after the coordinate transformation are given by (X', Y', Z').

Then in step S14, each of the combination of X' and Y' in the coordinate system, after the coordinate transformation, is scanned while changing the position of the Z axis from the positive direction to the negative direction, and the coordinates of a voxel, where the values are first received (in other words, a voxel where a signal exists) are recorded. Thereby the data representing the surface shape of the object (hereafter called "shape data") can be acquired.

Figure 3:
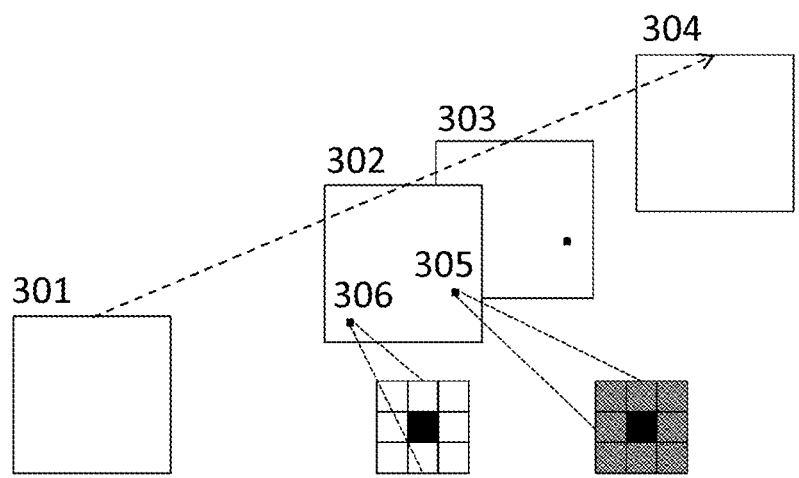
FIG. 3 is a diagram depicting processing to acquire the surface shape of an object.

An example of the method of acquiring the coordinates on the object surface will be described with reference to FIG. 3.

The reference numbers 301 to 304 indicate the state of the movement of the X'-Y' plane in the Z' axis direction. In the case of FIG. 3, the coordinates of the Z axis decrease moving from reference number 301 to 304.

Here it is assumed that a signal was observed at a position of the voxel 305 in the state of the reference number 302. In this case, the coordinates on the object surface in the three-dimensional space is determined by adding the Z' coordinate to the coordinates of the voxel 305. By performing this processing for all the voxels on the X'-Y' plane, the three-dimensional shape data of the object surface can be acquired.

If no signal is observed in the adjacent voxels of a voxel where a signal is observed (e.g. voxel 306), this voxel is handled as a voxel where a signal is not observed. This processing is performed to remove noise. In other words, a position where a signal is observed continuously from adjacent voxels is regarded as the surface of the object. For example, the data processing unit 108 regards that the surface of the object exists when the difference of the voxel values among adjacent voxels is smaller than a predetermined value.

Here a case when the shape data of the object is acquired using the photoacoustic signal was shown, but the shape data may be acquired by other means. For example, data measured by ultrasound, nuclear magnetic resonance, X-rays or the like may be used as the shape data of the object.

If the shape shown in the acquired shape data is different from the shape of the object when the photoacoustic signal was acquired, the data processing unit 108 may correct the shape data. In other words, the data processing unit 108 may correct the shape data so that the shape represented by the acquired shape data corresponds to the shape of the object when the photoacoustic signal was acquired. For example, the data processing unit 108 may transfer the shape shown by the shape data using affine transformation or the like, and acquire the shape data representing the shape after the transformation.

Description is continued referring to FIG. 2 again.

In step S15, a distance to the object surface is determined for each voxel existing inside the object (inner side of object surface). The distance determined here is called a "voxel depth". The distance between the object surface and a voxel is the distance in the normal line direction from the object surface.

Then in step S16, filtering processing is performed for the value of each voxel using a corresponding voxel depth. Here the following two methods will be described as examples of the filtering method. A filtering other than these examples may be used instead.

(1) The filtering processing is performed so that the voxel value decreases as the voxel depth increases.

According to this method, the value corresponding to the voxel decreases (brightness when converted into the two-dimensional image decreases) as the position departs from the object surface (e.g. human skin) in the depth direction (in other words, as the position departs from the viewpoint of the user). For example, filtering processing that decreases the weight for a voxel value as the voxel depth increases, may be applied.

(2) The filtering processing is performed so that the intensity of a blur increases as the voxel depth increases.

According to this method, filtering processing is performed such that, for instance, values corresponding to the voxels more strongly scatter (the intensity of a blur when converted into the two-dimensional image increases) as the position departs from the object surface in the depth direction. For example, the blur radius is changed based on the distance from the object surface by applying Gaussian blurring, so that the image of the voxel is more strongly blurred as the distance of the voxel from the object surface is longer. In other words, the radius in the Gaussian distribution is increased as the distance from the object surface is longer, whereby the Gaussian distribution is convolved into the three-dimensional data.

Then in step S17, the two-dimensional image is generated using the filtered three-dimensional data by a desired rendering method, and is outputted to the displaying unit 109. The rendering method that can be used is, for example, a publically known rendering method, such as a maximum intensity projection method, a minimum intensity projection method, a volume rendering method and a surface rendering method.

For example, if the three-dimensional data after the filtering processing in the above (1) is projected by the maximum intensity projection method, a two-dimensional image, where transparency is high at a position of which voxel depth is large, can be displayed. If the three-dimensional data after the filtering processing in the above (2) is projected by the maximum intensity projection method, a two-dimensional image, where the degree of blur is high at a position of which voxel depth is large, can be displayed. Thus a two-dimensional image expressing depth can be displayed. As a result, a user, such as a physician, can diagnose while checking the two-dimensional image of which information in the depth direction can be easily distinguished.

In this embodiment, the filtering processing to change the voxel values of the three-dimensional data, such as the filtering processing in (1) or (2), is used. However, besides these filtering processing operations, any filtering method may be used as long as transparency or the degree of blur can be changed in accordance with the voxel depth.

After the filtered three-dimensional data is stored in the memory, the two-dimensional image may be generated by projecting the filtered three-dimensional data stored in the memory. The filtering processing may be performed when the three-dimensional data is projected. This processing also corresponds to the processing to generate the two-dimensional image based on the filtered three-dimensional data.

Figure 4:
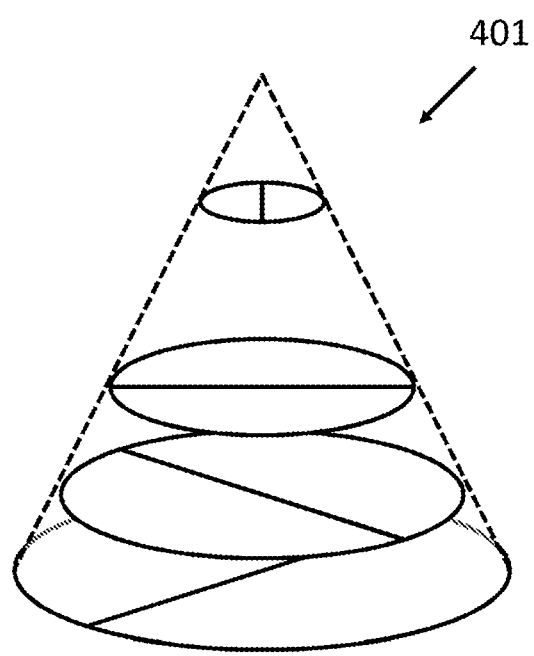
FIG. 4 is a diagram depicting an example of the object.

Here an example of the photoacoustic measurement performed on a conical object 401, as illustrated in FIG. 4, and the filtering processing performed on the generated three-dimensional data will be described. In the object 401, four linear light absorbers, which are parallel with the bottom face, and four circular light absorbers along the surface, are disposed. In this example, the photoacoustic measurement is performed regarding the apex side of the object as the front side, and the bottom surface side of the object as the rear side.

Figure 5:
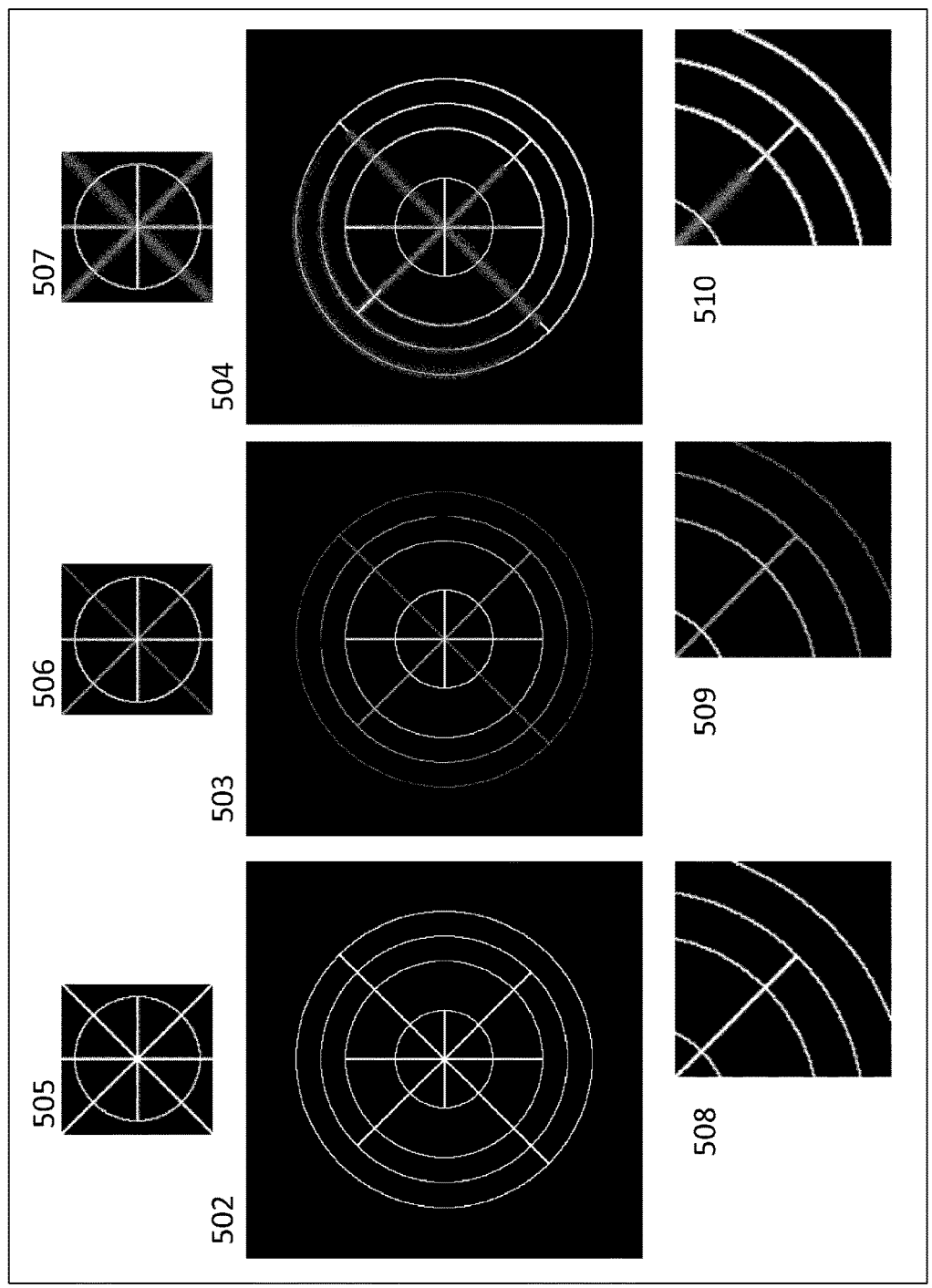
FIG. 5 is a result of measuring the object.

An image 502 illustrated in FIG. 5 is an image generated by converting the acquired three-dimensional data into the two-dimensional image using the conventional maximum intensity projection method. In the image 502, all lines are drawn at the same brightness. An image 503 is an image generated by converting the three-dimensional data into the two-dimensional image using the conventional volume rendering method. In the image 503, the brightness of the line is changed depending on the distance from the viewpoint.

An image 504 is an image generated by converting the acquired three-dimensional data into the two-dimensional image using the method according to the present invention. In the image 504, a blur filter is applied to each voxel based on the distance from the closest object surface. The three-dimensional voxels, to which the blur filter is applied like this, are displayed as the two-dimensional image using the maximum intensity projection method.

Images 505, 506 and 507 are enlarged views of the center portions of the images 502, 503 and 504 respectively. As these images show, the positional relationship of the light absorbers cannot be recognized in the image 505. In the images 506 and 507, on the other hand, the positional relationship of the light absorbers can be recognized.

In the same manner, images 508, 509 and 510 are enlarged views of the lower right portions of the images 502, 503 and 504 respectively. As these images show, the depth of the light absorbers (distance from the surface) can be more easily recognized in the image 510, compared with the images 508 and 509.

In the case of FIG. 5, the processing to enhance the light absorbers located close to the surface of the object and blur the light absorbers located deep in the object was performed, to indicate the positional relationships of the object surface and the light absorbers, but other methods may be used. For example, filtering processing that provides lower brightness to a light absorber located in a deeper area of the object, and provides a higher brightness to a light absorber located closer to the surface, may be performed.

Figure 6:
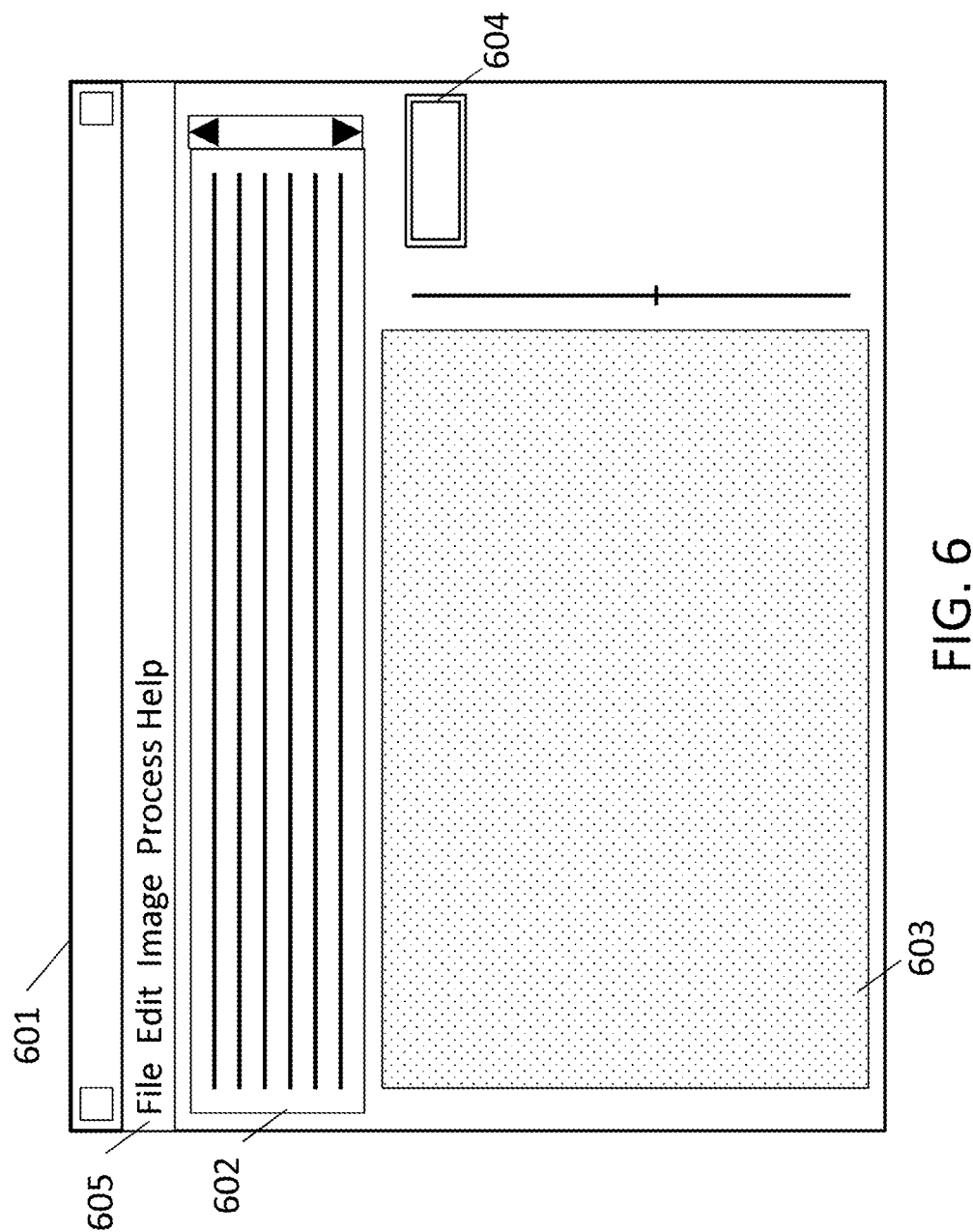
FIG. 6 is an example of a screen provided to the user.

FIG. 6 is an example of a user interface which is displayed on the display unit 109. This user interface is displayed by a window system, which is operated using such a pointing system as a mouse.

The list display section 602, in which the acquired photoacoustic signals are displayed as a list for each object, and an image display section 603, in which the photoacoustic signal is imaged and displayed, are disposed in window 601. A switch button 604, to change the method of displaying an image in the image display section, is also disposed.

A photoacoustic image corresponding to an object selected in the list display section 602, is displayed in the image display section 603. A two-dimensional object image, generated by an image processing method selected by the switch button 604, is displayed in the image display section 603.

In this embodiment, an arbitrary image processing method can be selected by pressing the switch button 604. The selectable image processing methods are, for example: displaying three cross-sections of a tomographic image; the two-dimensional projection of a volume rendering data; the maximum intensity projection method; and the display method according to the present invention.

The list display section 602 and the image display section 603 may be disposed in the same window, or may be disposed in different windows. The button to select the image processing method need not be disposed in a window, as in the case of the switch button 604. For example, the button may be disposed in a menu 605 attached to the window.

In this embodiment, the image displayed on the image display section 603 can be rotated using a pointing device or the like. Here if a certain direction is determined as the front face, the three-dimensional data is converted into a two-dimensional image using the method selected by the switch button 604. If the method according to the present invention is selected by the switch button 604, the coordinate transformation in accordance with the determined orientation is performed in step S13.

Embodiment 2

Embodiment 2 is an embodiment in which a human breast is measured using a hemispherical acoustic wave probe, and blood vessels inside the breast are visualized. In an object information acquiring apparatus according to Embodiment 2, the oxygen saturation distribution inside the breast is acquired by performing measurement using a plurality of wavelengths. Thereby the positions of the arteries and veins inside the breast can be determined.

Figure 7:
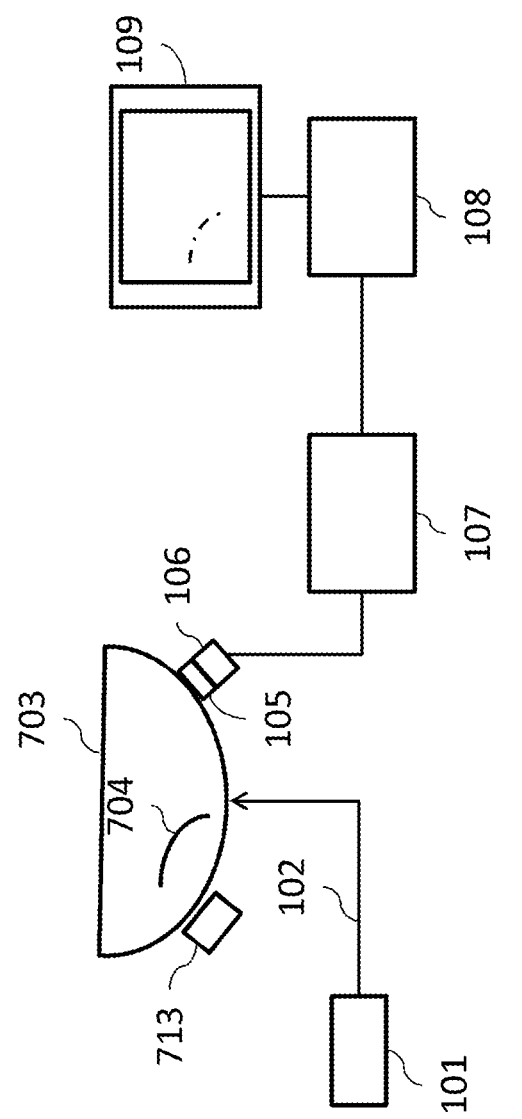
FIG. 7 is a diagram depicting functional blocks of an object information acquiring apparatus according to Embodiment 2.

In Embodiment 2, the acoustic wave probe 106 is installed in a hemispherical support member. In the example in FIG. 7, the acoustic wave probe is installed in a part of the support member, but the acoustic wave probe 106 may be movable on the support member. Further, the acoustic wave probe 106 may be constituted by a plurality of acoustic elements which are dispersed inside the support member.

The rest of the configuration is the same as Embodiment 1, therefore description thereof is omitted.

When the pulsed light is emitted from the light source 101 to the breast 703 (corresponding to the object 103) via the optical system 102, the light is absorbed by red blood cells 704 (corresponding to the absorbers 104) inside the blood vessels.

The red blood cell 704 contains oxyhemoglobin and deoxyhemoglobin, and the absorption amount is different depending on the wavelength of the irradiated light. Utilizing this feature, the oxygen saturation distribution inside the object can be acquired by irradiating light of a plurality of wavelengths from the light source 101. A plurality of wavelengths here are two types of wavelengths: 756 nm and 797 nm, for example.

The photoacoustic wave acquired from the red blood cells 704 reaches the acoustic wave probe 106 via the acoustic matching material 105, and is converted into an electric signal (photoacoustic signal). The acquired photoacoustic signal is transmitted to the data processing unit 108 via the signal processing unit 107.

The data processing unit 108 calculates the oxygen saturation degree for each voxel using a photoacoustic signal acquired for each of the plurality of wavelengths.

After acquiring the shape data of the breast 703, the distance between the voxel in which the photoacoustic signal was detected and the object surface is calculated, and the filtering processing is performed for each voxel based on the calculated distance. In concrete terms, for a voxel of which distance from the skin surface is long, transparentizing processing is performed. If signals exist in voxels overlapping in the depth direction respectively in the filtered image, this means that the voxels located in the deeper position have been transparentized, hence a two-dimensional image having a good three-dimensional effect is outputted to the displaying unit 109 by projecting only the voxels located close to the object surface.

The red blood cells 704 exist in blood flowing through blood vessels, which means that an image of the blood vessels can be drawn by imaging the red blood cells inside the breast. Further, the oxygen saturation distribution inside the blood vessel can be acquired by calculating the oxygen saturation degrees using a plurality of wavelengths, whereby it can be detected whether a blood vessel in the region of interest is an artery or a vein.

To distinguish whether a blood vessel is an artery or a vein in an image acquired by the photoacoustic measurement, it is critical that the continuity of the blood vessel can be easily recognized. If the two-dimensional image is generated by the method according to this invention, the depth of the object tissue, the continuity of the blood vessel, and how blood vessels overlap can be determined. In other words, whether the imaged blood vessel is an artery or a vein can be easily discerned.

In this embodiment, the filtering processing may be executed for each of a plurality of three-dimensional data corresponding to a plurality of wavelengths first, so that the oxygen saturation distribution is calculated based on the plurality of three-dimension data generated after the filtering processing. In this case, different filtering processing operations may be used for each of the plurality of three-dimensional data. For example, the absorption of melanin increases at a shorter wavelength, which decreases the amplitude of the acoustic wave generated in a deep region, and may cause a drop in image quality in a deep region. To prevent this, the intensity of a blur may be increased or the brightness may be decreased as the distance from the surface increases for a three-dimensional data corresponding to the shorter wavelength, compared with the case of a longer wavelength. Then the variance of image quality of the three-dimensional data among wavelengths can be decreased.

A unit to measure a shape of an object may be added to Embodiment 2. For example, a detecting device 713, which transmits an ultrasonic wave to the object and acquires the shape of the object based on the reflected wave, may be added.

Other Embodiments

The description of each embodiment is an example of describing the present invention, and the present invention can be carried out by changing or combining the above embodiments within a scope of not departing from the essence of the invention.

For example, the present invention may be implemented as an object information acquiring apparatus that executes at least a part of the above processing operations. The present invention may also be implemented as an object information acquiring method that includes at least a part of the above processing operations.

Further, the present invention may be implemented as an image processing apparatus that performs image processing on the three-dimensional data acquired by the object information acquiring apparatus. The present invention may also be implemented as an image processing method performed by the image processing apparatus.

These processing operations and units may be freely combined as long as no technical inconsistency is generated.

In the description of the embodiments, the filtering processing, to enhance visibility (to increase the correction amount to correct a value) as the target voxel is closer to the object surface was described as an example, but other filter processing operations may be used if the intensity of filtering is determined based on the distance from the object surface. For example, the correction amount to correct the value may be increased as the position of the voxel is deeper in the object.

"A plurality of voxels" in the present invention need not include the entire region of the acquired three-dimensional data. For example, the filtering processing described in the embodiments may be performed only for a part of the voxels constituting the acquired three-dimensional data. For the rest of the voxels, the result of the filtering processing may be reflected (e.g. performing interpolation).

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-061164, filed on Mar. 27, 2017, which is hereby incorporated by reference herein in its entirety.

What is claimed is:

1. An image processing apparatus, comprising:
   an information acquiring unit that acquires three-dimensional data representing characteristic information on an object at a plurality of voxels;
   a shape information acquiring unit that acquires information on a surface shape of the object;
   a distance calculating unit that calculates, for each of the voxels, a distance between a surface of the object and a position inside the object corresponding to the voxel, based on the information on the surface shape;
   a filtering unit that performs, for each of the voxels, filtering processing, including blur processing in accordance with the calculated distance; and
   an image generating unit that generates a two-dimensional image, based on the three-dimensional data after the filtering processing.

2. The image processing apparatus according to claim 1, wherein
   the filtering unit performs the filtering processing for each of the voxels, so that an intensity of the blur is higher as the distance from the surface of the object is longer.

3. The image processing apparatus according to claim 1, wherein
   the image generating unit generates the two-dimensional image by projection, by using the three-dimensional data after the filtering processing.

4. The image processing apparatus according to claim 1, wherein
   the shape information acquiring unit acquires the information on the surface shape of the object by performing processing that regards a position, in which a signal is observed continuously from the adjacent voxels, as a surface of the object.

5. The image processing apparatus according to claim 1, wherein
   the three-dimensional data is data generated based on an acoustic wave which was generated by light irradiated to the object.

6. The image processing apparatus according to claim 5, wherein
   the three-dimensional data includes a plurality of three-dimensional data corresponding to irradiated light of a plurality of wavelengths, and
   the filtering unit performs mutually different filtering processing operations for the plurality of three-dimensional data respectively.

7. The image processing apparatus according to claim 6, wherein
   the filtering unit performs filtering processing for the plurality of three-dimensional data, so that the intensity of the blur increases as the wavelength of the irradiated light is shorter.

8. An image processing method, comprising:
   an information acquiring step of acquiring three-dimensional data representing characteristic information on an object at a plurality of voxels;
   a shape information acquiring step of acquiring information on a surface shape of the object;
   a distance calculating step of calculating, for each of the voxels, a distance between a surface of the object and a position inside the object corresponding to the voxel, based on the information on the surface shape,
   a filtering step of performing, for each of the voxels, filtering processing, including blur processing in accordance with the calculated distance; and
   an image generating step of generating a two-dimensional image, based on the three-dimensional data after the filtering processing.

9. The image processing method according to claim 8, wherein
   in the filtering step, the filtering processing is performed for each of the voxels, so that an intensity of the blur is higher as the distance from the surface of the object is longer.

10. The image processing method according to claim 8, wherein
    in the image generating step, the two-dimensional image is generated by projection, by using the three-dimensional data after the filtering processing.

11. The image processing method according to claim 8, wherein
    in the shape information acquiring step, the information on the surface shape of the object is acquired by performing processing that regards a position, in which a signal is observed continuously from the adjacent voxels, as a surface of the object.

12. The image processing method according to claim 8, wherein
    the three-dimensional data is data generated based on an acoustic wave generated by light irradiated to the object.

13. The image processing method according to claim 12, wherein
    the three-dimensional data includes a plurality of three-dimensional data corresponding to irradiated light of a plurality of wavelengths, and
    in the filtering step, mutually different filtering processing operations are performed for the plurality of three-dimensional data respectively.

14. The image processing method according to claim 13, wherein
    in the filtering step, filtering processing is performed for the plurality of three-dimensional data so that the intensity of the blur increases as the wavelength of the irradiated light is shorter.

15. A non-transitory computer readable storing medium recording a computer program for causing a computer to perform an image processing method comprising:
    an information acquiring step of acquiring three-dimensional data representing characteristic information on an object at a plurality of voxels;
    a shape information acquiring step of acquiring information on a surface shape of the object;
    a distance calculating step of calculating, for each of the voxels, a distance between a surface of the object and a position inside the object corresponding to the voxel, based on the information on the surface shape,
    a filtering step of performing, for each of the voxels, filtering processing, including blur processing in accordance with the calculated distance; and
    an image generating step of generating a two-dimensional image, based on the three-dimensional data after the filtering processing.

* * * * *